United States Patent [19]

Fedotov et al.

[11] 4,290,542
[45] Sep. 22, 1981

[54] SURGICAL INSTRUMENT FOR STAPLE SUTURING OF ORGANS

[76] Inventors: Vladimir M. Fedotov, ulitsa Startovaya, 21, kv. 42; Boris A. Smirnov, ulitsa Borisa Galushkina, 17, kv. 26; Genrikh I. Lukomsky, pereulok Chisty, 5A, kv. 35, all of Moscow; Iosif L. Lipovsky, proezd Ozerkovsky, 7, kv. 32, Leningrad, all of U.S.S.R.

[21] Appl. No.: 105,860

[22] Filed: Dec. 20, 1979

[30] Foreign Application Priority Data

Dec. 25, 1978 [SU] U.S.S.R. .................... 2714120

[51] Int. Cl.³ .............................................. A61B 17/04
[52] U.S. Cl. .................................. 227/155; 128/334 R; 128/305; 227/19; 227/DIG. 1
[58] Field of Search ............... 128/334 R, 326, 325, 128/321, 346, 305; 72/410; 227/19, DIG. 1, DIG. 1 A, DIG. 1 B, 144, 155; 29/243.56

[56] References Cited

U.S. PATENT DOCUMENTS

| 3,079,608 | 3/1963 | Babkin | 227/19 X |
| 4,111,206 | 9/1978 | Vishnevsky et al. | 128/334 R X |

FOREIGN PATENT DOCUMENTS

| 927936 | 6/1963 | United Kingdom | 128/334 R |
| 571948 | 3/1977 | U.S.S.R. | 128/305 |

Primary Examiner—Lee S. Cohen
Assistant Examiner—Michael H. Thaler
Attorney, Agent, or Firm—Fleit & Jacobson

[57] ABSTRACT

Described herein is an instrument, having detachably hinged together supporting and staple bodies provided with parallel-arranged jaws, of which one jaw is adapted for carrying staple magazines, while the other, for accommodating therein a slidable member provided with recesses for bending staples. The slidable member is adjustably traversable towards the staple body and can be locked in a preset position. A device is provided for imparting the above motions to the slidable member.

2 Claims, 6 Drawing Figures

SURGICAL INSTRUMENT FOR STAPLE SUTURING OF ORGANS

FIELD OF THE INVENTION

The present invention relates to medical equipment and is concerned more specifically to a surgical instrument for staple suturing of organs, e.g., for establishing lateral gastrointestinal and intestinal anastomoses, and also for suturing organs, involving application of staple sutures both to the remaining portion of the organ operated upon and to its portion to be ablated, and simultaneous severing of the latter portion.

BACKGROUND OF THE INVENTION

The present state of the art knows a surgical suturing instrument disclosed in USSR Inventor's Certificate No. 571,948, which comprises a staple body with a jaw and a grip, a change magazine provided with staple slots and situated in the staple body, staple ejectors provided with stops and located in the magazine staple slots, a supporting body with a jaw provided with recesses for the staple to bend. The instrument has also a device for advancement of the staple ejector with a knife, and a mechanism for interlocking the staple and supporting bodies. This instrument is designed predominantly for stitching up organs through manipulating in a narrow and deep operative wound, and cannot be employed for establishing lateral gastrointestinal and intestinal anastomoses or, if anything, such an application of the instrument is to the utmost difficult to carry out, as according to the adopted application techniques, the instrument jaws can be introduced into the organs being sutured through the operative wound only when having been disjoined into the two halves. Since the staple and supporting bodies in the instrument under consideration are kinematically associated through the interlocking mechanism, they may not be disjoined during operation. In addition, with such a constructional arrangement of the instrument its overall length is so great that it offers much difficulties when manipulating the instrument in the operative wound to establish gastrointestinal and intestinal anastomoses.

These disadvantages have partially been obviated in the instrument disclosed in U.S. Pat. No. 3,079,608.

The instrument is known to comprise detachably hinged a supporting and a staple bodies, both having respective parallel-arranged jaws with recesses for staples to bend and for the staple magazine to fit, a staple ejector and a rack-type locking device to fix the bodies in position with respect to each other. However, this instrument also suffers from a number of disadvantages largely stemming from the fact that the instrument is practically devoid of adjusting the suturing gaps.

It is due to different wall thickness of the organs of the gastrointestinal tract in various patients that the range of suturing gaps required for the suturing instruments covers 2.3 mm, varying within 0.4 to 2.7 mm. With such wide variations of the wall thickness of the organs to be sutured the instruments having a constant suturing gap, fail to provide optimum forces of compression and suturing of the walls of the organs.

When suturing thick-walled organs with the instrument under discussion, the walls are unnecessarily injured, and the obtained sutures are oftentimes inadequately haemostatic.

Furthermore, the abovesaid constructional arrangement of the instrument fails to provide a possibility for increasing the suturing gaps, as this will affect very badly the quality of the suture for its length owing to a mutually unparallel travelling of the instruments jaws compressing the tissue being sutured.

The gap effective in between the surfaces of the instrument jaws that compress the tissue being sutured, is in fact shaped as a radial sector; that is why the distance between the compressing jaw surfaces is shorter at the base of the jaws than at their ends, and the difference in that distance becomes greater with an increase in the gap. All this leads not only to an inadequate compression of the tissues being sutured but also to a nonuniform height of the staple suture obtained, i.e., to the formation of a poor-quality suture.

It is an essential object of the present invention to provide a uniform compression of the suture through its length within a broad range of suturing gaps involved in establishing lateral gastrointestinal and intestinal anastomoses.

It is another object of the present invention to improve the quality and reliability of the suture obtained.

Among the other objects of the present invention there are worth noting a considerably diminished degree of injury to the organs being sutured, and an uneventful healing of the tissues operated upon during the postoperative period.

The abovesaid and other objects are accomplished due to the fact, that in a surgical instrument for staple suturing of organs, comprising detachably hinged a supporting and a staple bodies, both having respective parallel-arranged jaws with recesses for staples to bend and for the staple magazine to fit, as well as a staple ejector and a retainer to hold the bodies in position with respect to each other, according to the invention, the jaw of the supporting body has a slidable member capable of adjustably traversing towards the staple body and of being locked in a preset position, said slidable member having a number of recesses for staples to bend and incorporating a device to impart adjusting motion to the abovesaid slidable member.

Provision of a slidable member enables one to adjust the jaw-to-jaw gap so as to ensure a uniform compression of the suture throughout its length within a broad range of the suturing gaps. This, in turn, is conducive to higher quality and reliability of the suture obtained, greatly reduces the degree of injury to the organ tissues involved in surgery and provides for an uneventful healing of the tissues within the postoperative period.

In one of the embodiments of this invention a longitudinal slot is made in the bulk of the jaw to accommodate a bar adjustably slidable along the abovesaid slot.

In order to impart motion to the above bar, a crank-shaft is provided, the journals of which are made fast on the supporting body, and its throw is accommodated in a slot provided in the bar.

One of the crank-shaft journals is expedient to be provided with a lever having a lock to fix the crank-shaft in position after its turning.

BRIEF DESCRIPTION OF THE DRAWINGS

In order that the present invention may be more readily understood, a specific embodiment thereof will be described by way of example and with reference to the accompanying drawings, wherein.

DETAILED DESCRIPTION

Figure 1:
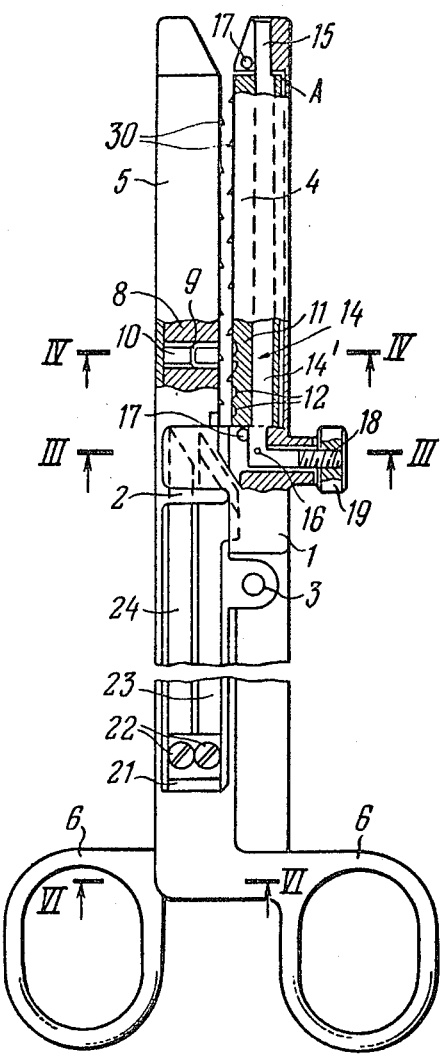
FIG. 1 is a general, fragmentarily cutaway view of the instrument, according to the present invention.
Figure 2:
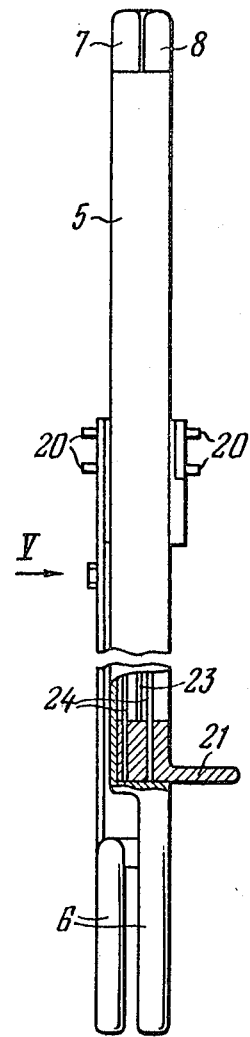
FIG. 2 is a side-elevation view of the instrument as shown in FIG. 1.
Figure 3:
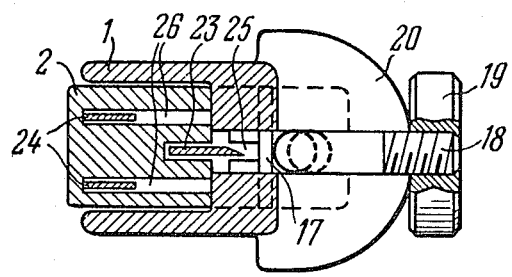
FIG. 3 is a section taken along the line III—III in FIG. 1.
Figure 4:
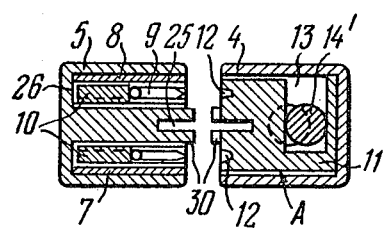
FIG. 4 is a section taken along the line IV—IV in FIG. 1.
Figure 5:
FIG. 5 is a view facing the arrow V in FIG. 2.
Figure 6:
FIG. 6 is a section taken along the line VI—VI in FIG. 1.

The surgical instrument for staple suturing of organs comprises a supporting body 1 and a staple body 2 (FIGS. 1, 2 and 3), which are hinge-joint through a pivot pin 3 (FIGS. 1 and 2) so as to be disjoined from each other. The bodies 1 and 2 have respective jaws 4 and 5 at one of their ends and are provided with rings 6 at the other end. Detachably mounted on the jaw 5 of the staple body 2 are staples magazines 7 and 8 with staples 9 and ejectors 10 for the staples 9. A slot A is made in the jaw 4 of the supporting body 1, said slot accommodating a bar 11 having recesses 12 for the staples 9 to bend, which bar 11 being traversable crosswise in said slot, i.e., towards the staple body and away from it. A longitudinal slot 13 is made in the bar 11, which accommodates a crank throw 14' of the shaft 14 having journals 15 and 16 (FIGS. 1, 3 and 4). The crankshaft 14 is made fast on the supporting body 1 by pins 17. The journal 16 has a lever 18 with a threaded end on which a roller 19 is screwed, adapted to contact radial lugs 20 (FIG. 3) provided on the supporting body 1 to keep the shaft 14 against spontaneous rotation. Crank throw 14' has an axis off-set from the axis of the journal 16 so that rotation of journal 16 by rotation of lever 18 results in the crank throw 14' engaging the bar 11 and either moving the bar into or out of the slot A in jaw 4. A slider 21 is provided on the staple body 2, to which a plate knife 23 and strips 24 with wedge-shaped bevels are held with screws 22, said strips being traversable along narrow slots 25 and 26 (FIGS. 3 and 4). The hinge pin 3 has at one of its ends claws 27 adapted to engage respective slots 28 (FIG. 5) in the supporting body 1 to form a single-lug lock along with the supporting body 1 and the staple body 2. When brought together the supporting body 1 and the staple body 2 are fixed in place by a rack-type lock 29 (FIG. 6). To prevent the tissue from being dragged when out by the knife 23, serrations 30 (FIGS. 1 and 4) are provided on the compression surfaces of the jaws 4 and 5.

Now reference will be directed to the operation of the surgical instrument for staple suturing of organs, according to the present invention.

Having lightly backed off the roller 19 one must turn the lever 18 of the crank-shaft 14 to the rightmost position to slide the bar 11 having the recesses 12, into the jaw 4 of the supporting body 1, thereby setting the instrument to a position, corresponding to a maximum suturing gap. Next the supporting body and the staple body 2 are disjoined, whereupon the jaws 4 and 5 of the instrument bodies are introduced completely into the lumina of the organs being sutured by gaining access through the appropriate incisions in the walls of the organs involved, viz., the jaw 4 of the supporting body 1 is brought into the gastric lumen, while the jaw 5 of the staple body 5 is introduced into the lumen of the small intestine. Then the supporting body 1 and the staple body 2 are joined by bringing together the rings 6 till the bodies are held to each other by the rack-type lock 29. This done, one must turn the crank-shaft 14 to the left by the lever 18 so as to uniformly compress the walls of the organs being sutured till a gap is obtained to provide application of a tight suture. Having turned the roller 19 till a tight contact of its inner surface with the surfaces of the radial lugs 20, one thus ensures against spontaneous rotation of the crank-shaft. Thereupon the slider 21 carrying the plate knife 23 and the strips 24 with wedge-shaped bevels, is moved along the staple body as body as far as it will go, with the result that the strips 24 with their wedge-shaped bevels actuate the ejectors 10, which drive the staples 9 out of their respective slots. Having left the slots of the magazines 7 and 8, the staples 9 with their pointed legs prick the walls of the organs and thrust against the walls of the recesses 12 in the bar 11, thus getting bent into B-shape to form a suture. Concurrently with advancement of the strips 24 having wedge-shaped bevels, the knife 23 severs the tissue between the sutures being applied, thus establishing communication between the gastric stump and the enteric loop. This done, the slider 21 is returned into the initial position, the jaws 4 and 5 are brought apart and withdrawn from the lumina of the sutured organs. Further manipulations involved in stitching up the incisions and forming a purse suture are performed manually in keeping with the adopted techniques.

For a next application of the instrument for staple suturing to stitch together or stitch up organs, the empty magazines must be replaced by the loaded ones.

In order to modify the suturing gap, one must turn the crankshaft so as to change the distance between the bar and the staple body jaw.

As to its constructional arrangement and application techniques the instrument disclosed in the present invention is convenient in handling and is readily mastered by a surgeon, provides for a range of the suturing gaps broad enough to be applicable practically for suturing any soft human tissues, and may be employed for stitching up or stitching together the organs of the alimentary tract, suturing blood vessels, or for a variety of plastic and reconstructive operations.

What we claim is:

1. A surgical instrument for staple suturing of organs, comprising a supporting body, a staple body, a hinge joint for detachably articulating said supporting and staple bodies together, a jaw provided on the staple body and adapted for carrying removable staple magazines, the staple magazines accommodating staples for suturing and staple ejector means reciprocatingly mounted in the staple magazines for driving staples out of the magazines, a jaw having a lengthwise recess formed therein provided on the supporting body, a slidable member arranged in the lengthwise recess of said jaw of the supporting body for movement with respect to said supporting body so as to perform translating adjusting motion in a transverse direction with respect to the staple body for adjusting a gap between the slidable member and the staple body jaw, said slidable member having a surface thereof arranged parallel to the staple body jaw when the supporting body and staple body are in a stapling position, retainer means for fixing said slidable member in a preset position during adjusting motion thereof, recesses for bending staples formed in said slidable member, and actuator means for imparting adjusting motion to the slidable member wherein said actuator means comprises a crankshaft having journals held by the supporting body and a crank throw positioned between the journals, said slidable member having a slot formed therein to accommodate the crank throw, the crank throw being eccentric with respect to one of the journals so that rotation of the one journal results in translation of the slidable member by the crank throw.

2. An instrument as claimed in claim 1, wherein said actuator means comprises a lever connected to said one of the journals, and means for locking the lever to thereby fix the crank-shaft in position after turning.

* * * * *